Figure 1:
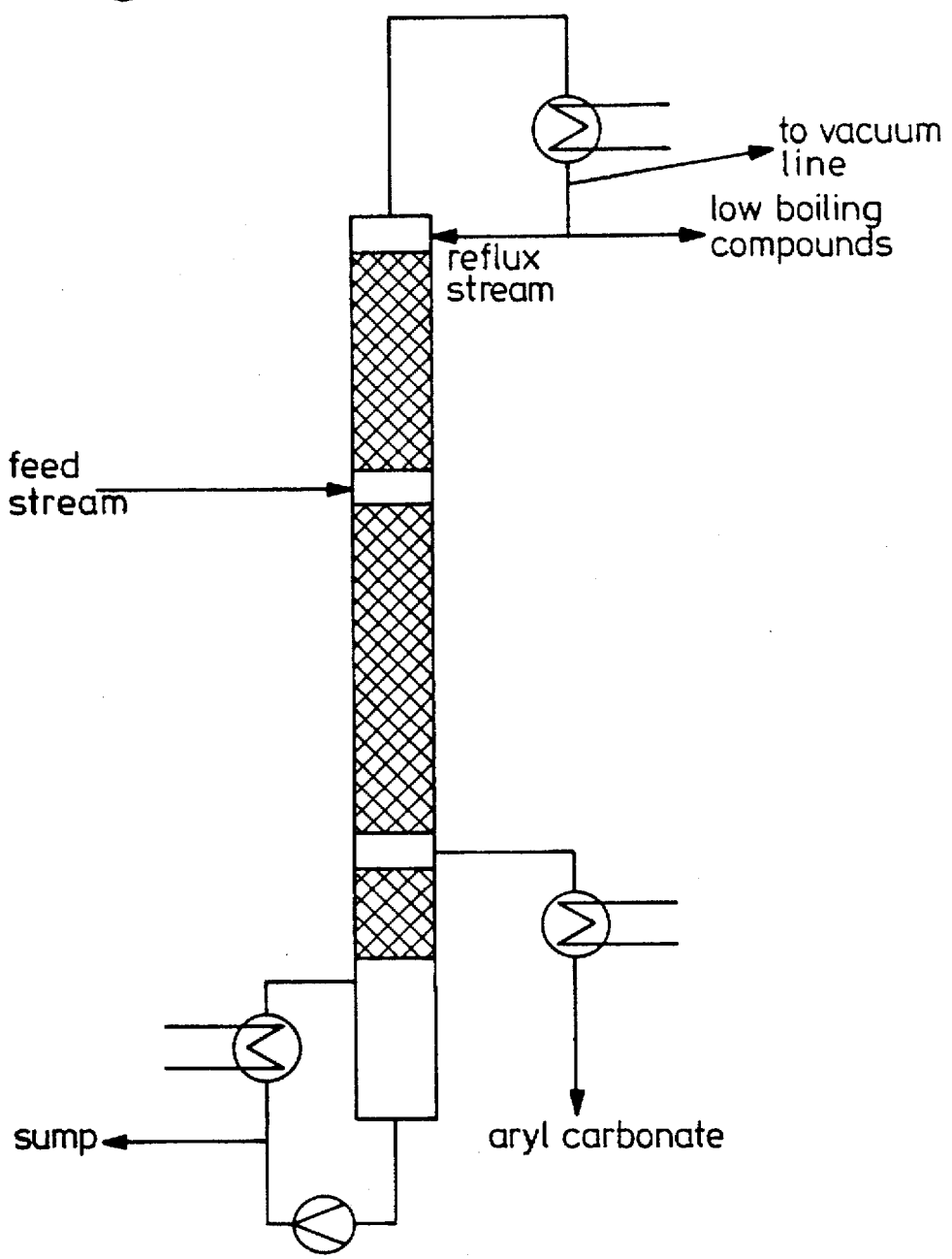

United States Patent [19]
Kühling et al.

[11] Patent Number: 5,734,004
[45] Date of Patent: Mar. 31, 1998

[54] PROCESS FOR THE PURIFICATION OF CARBONIC ACID DIARYL ESTER

[75] Inventors: Steffen Kühling, Meerbusch; Kaspar Hallenberger, Leverkusen; Pieter Ooms, Krefeld; Hans-Josef Buysch, Krefeld; Günther Jeromin, Krefeld, all of Germany

[73] Assignee: Bayer Aktiengesellschaft

[21] Appl. No.: 778,843

[22] Filed: Jan. 6, 1997

[30] Foreign Application Priority Data

Jan. 10, 1996 [DE] Germany .................. 196 00 631.7

[51] Int. Cl.$^6$ .................................................. C08G 64/00
[52] U.S. Cl. ........................... 528/196; 528/198; 202/182
[58] Field of Search ........................ 202/182; 528/196, 528/198

[56] References Cited

U.S. PATENT DOCUMENTS 5,336,376  8/1994  Taurat et al. .................... 202/182

FOREIGN PATENT DOCUMENTS

| 0 483 632 A2 | 5/1992 | European Pat. Off. . |
| 0 633 241 | 1/1995 | European Pat. Off. . |
| 42 14 738 A1 | 11/1993 | Germany . |

OTHER PUBLICATIONS

Encyclopedia of Polymer Science, vol. 10 (1969), Chemistry and Physics of Polycarbonates, Polymer Reviews, H. Schnell, vol. 9, John Wiley and Sons, Inc. (1964) pp. 50/51, 724.

*Primary Examiner*—Terressa Mosley
*Attorney, Agent, or Firm*—Connolly & Hutz

[57] ABSTRACT

The present invention relates to a distillation process for the purification of carbonic acid diaryl esters.

8 Claims, 1 Drawing Sheet

5,734,004

PROCESS FOR THE PURIFICATION OF CARBONIC ACID DIARYL ESTER

The present invention relates to a process for the purification of carbonic acid diaryl esters by continuous distillation, wherein the carbonic acid diaryl ester is distilled at bottom temperatures of >150° C. and collected in the side stream from the vapour phase of a column.

In the preparation of polycarbonates from carbonic acid diaryl esters and diphenols by the transesterification process, a consistently high quality of the carbonic acid diaryl ester is extremely important for a good quality of the resulting polycarbonate and for conducting the reaction and catalysing the process without difficulty. The purification, by distillation, of carbonic acid diaryl esters that were prepared by reaction of monophenols and phosgene in a solvent in the presence of alkali in the interface is described in the Encyclopedia of Polymer Science, Vol. 10 (1969), Chemistry and Physics of Polycarbonates, Polymer Reviews, H. Schnell, Vol. 9, John Wiley and Sons, Inc. (1964), page 50/51.

It has now been found that by means of a controlled continuous distillation process, the carbonic acid diaryl esters have an improved quality which makes them particularly suitable for polycarbonate preparation by the melt transesterification process.

Carbonic acid diesters within the meaning of the present invention are di-$C_6$–$C_{20}$-aryl esters, preferably the diesters of phenol or alkyl-substituted phenols, that is, diphenyl carbonate or e.g. dicresyl carbonate, but preferably diphenyl carbonate.

The carbonic acid diesters suitable for purification according to the process of the invention may have been prepared by various processes, for example, by means of the interfacial process (Encyclopedia of Polymer Science, Vol. 10 (1969), Chemistry and Physics of Polycarbonates, Polymer Reviews, H. Schnell, Vol. 9, John Wiley and Sons, Inc. (1964), the direct process from monophenol and carbonyl dihalide (described e.g. in EP-A 483 632), the carbonyl dihalide-free direct process from carbon monoxide and monophenol (e.g. DE-OS 27 38 437) and the transesterification process from dialkyl carbonates, particularly dimethyl carbonate and monophenols (e.g. JP-O-291 257, JP-O-93 660). The diesters prepared by the transesterification process or the direct process from monophenol and carbonyl dihalide are preferred since the purification process, apart from separating inorganic impurities, is particularly suitable for removing organic by-products from the carbonic acid diaryl ester. In the case of diphenyl carbonate, these may be phenyl chloroformate, 2-phenoxybenzoic acid, chlorinated aryl carbonates, xanthone, but in particular phenyl salicylate. The separation of phenyl salicylate is particularly problematic since the boiling points of diphenyl carbonate and phenyl salicylate are virtually the same.

The carbonic acid phenyl esters produced, for example, by the process described in EP-A 483 632 may contain 1200 to 7000 ppm of phenyl salicylate, depending on the test conditions.

Surprisingly, it has now been found that in spite of the very small difference in boiling points, the organic constituent content, particularly of phenyl salicylate, may be reduced to <1000 ppm, preferably <800 ppm, particularly preferably <500 ppm and in special preference <300 ppm in a continuous distillation operation by removing the carbonic acid diaryl ester in a side stream.

The removal of a side stream in the vapour phase is known from the literature and described, for example, in patent DE 4 214 738.

In the process according to the invention, distillation is carried out continuously in such a way that the bottom temperature during distillation is >150° C. to 310° C., preferably >160° to 230° C. To this end, a pressure between 1 and 1000 mbar, preferably between 5 and 100 mbar, is carried in the column. The average residence time of the crude carbonic acid diaryl ester is between 1 and 10 minutes, depending on how the process is conducted. The average residence time of the bottom product in the distillation apparatus is between 1 min and several days under industrial conditions, depending on the type of evaporator. The product streams obtained are removed from the plant via barometric lines or by means of suitable pumps. The lines and equipment in contact with product are heated to temperatures above the product melting points. In order to achieve the necessary efficiency, the column should be packed with ordered medium vacuum packing, ordered sheet metal packing or random packings. Five to 15 theoretical stages with reflux ratios of 0.5 to 10 are used for the separation. The distillation principle is shown in FIG. 1.

The carbonic acid diesters purified in this way are characterised by high purity (GC>99.9%) and extremely good transesterification behaviour (1* $10^{31\ 4}$ mol-% catalyst, e.g. NaOH, are sufficient for starting transesterification), so a polycarbonate of excellent quality may be prepared.

The preparation of aromatic oligo-/polycarbonates by the melt transesterification process is known from the literature and has already been described, for example, in the Encyclopedia of Polymer Science, Vol. 10 (1969), Chemistry and Physics of Polycarbonates, Polymer Reviews, H. Schnell, Vol. 9, John Wiley and Sons, Inc. (1964) or U.S. Pat. No. 5,340,905.

EXAMPLES

Example 1

A column with a 0.5 m rectification section and a 1 m stripping section of ordered medium vacuum packing with an internal diameter of 50 mm was used for the distillation of the diphenyl carbonate prepared by the direct phosgenation process (compare FIG. 1). A steam distributor which was modified for the condensation of subliming products was used as the top of the column. Condensation took place with water at 80° C. As a rule, operations were carried out at an overhead pressure of 12 mbar, measured behind condensation. The overhead temperature was 155° C., the temperature at the side removal point was 160° C. The reflux ratio was adjusted to a value of 5. The adiabatic jacket of the column was aligned with the internal temperature. At a feed rate of 600 g/h, a distillate quantity of 30 g/h of low-boiling products was drawn off over the top. Below the stripping section, 570 g/h of carbonic acid diaryl ester were removed in the side stream. The GC product purity achieved in this way was 99.96%; at the same time, the phenyl salicylate content could be reduced from 3000 ppm in the crude product to concentrations of 200 ppm.

The diphenyl carbonate thus obtained undergoes a melt PC suitability test. The transesterification behaviour and thus the suitability of the carbonic acid diphenyl ester for melt transesterification is determined by the start temperature method. The reaction mixture of 17.1 g (0.075 mol) of 2,2-bis-(4-hydroxyphenyl)propane and 17.0 g (0.07945 mol) of the carbonic acid diphenyl ester to be tested is catalysed with 0.0001 mol-% of NaOH (based on BPA) (1% aqueous solution) and placed in a 100 ml flask with a bridge and thermometer in an oil bath pre-heated to 270° C. The start temperature and the time required by the mixture of starting products for transesterification and hence the onset of distillation (phenol splitting) are noted for comparison.

A requirement for good transesterification behaviour is that transesterification should begin even with low catalyst concentrations. This situation arises when the bottom temperature remains at <260° C. in the start temperature method, and the first phenol split off distils after <20 min.

The DPC purified by the above-mentioned process shows the first distillation after 14 min and at a bottom temperature of 255° C.

Example 2

Distillation was carried out in the same apparatus as in Example 1, but distillation was carried out at a column temperature of 210° C. and a correspondingly higher pressure. With the same quantity balance and feed concentration, the phenyl salicylate content could be reduced from 3000 ppm to concentrations of 50 ppm. The distilled DPC shows the first distillation after 13 min and at a bottom temperature of 253° C.

We claim:

1. A process for the purification of aromatic carbonic diesters in which aromatic carbonic diesters are continuously distilled in a distillation column having a bottom temperature of more than 150° C., and wherein product is removed in a side stream of the column, and producing aromatic carbonic diesters by a process selected from the group consisting of direct halogenation of monophenols in a melt, direct halogenation of monophenols in a gas phase, transesterification of monophenols with dimethyl carbonate, and reaction of carbon monoxide with monophenol.

2. A process according to claim 1, characterised in that the carbonic acid diesters purified in this way have a high GC purity of >99.9% and an extremely good transesterification behaviour when used in the preparation of polycarbonate.

3. A process according to claim 1, characterised in that the carbonic acid diester used is diphenyl carbonate.

4. A process according to claim 3, characterised in that the phenyl salicylate content is reduced to concentrations of <1000 ppm in the resulting diphenyl carbonate.

5. A process according to claim 4, characterised in that the phenyl salicylate content may be reduced to concentrations of <500 ppm in the resulting diphenyl carbonate.

6. A process for the preparation of polycarbonate in the melt, characterised in that a carbonic acid diester which was prepared according to claim 1, is used.

7. Carbonic acid diesters which are prepared by the process of transesterification or direct halogenation of monophenols in the melt or gas phase, distilled continuously at a bottom temperature of more than 150° C., removed in the side stream of the column and which then have a GC purity of >99.9% with a phenyl salicylate concentration of <1000 ppm and an extremely good transesterification behaviour.

8. Carbonic acid diesters according to claim 7 which have a phenyl salicylate concentration of <500 ppm.

* * * * *

UNITED STATES PATENT AND TRADEMARK OFFICE
CERTIFICATE OF CORRECTION

PATENT NO. : 5,734,004
DATED : March 31, 1998
INVENTOR(S) : Steffen Kuhling, et. al.

It is certified that error appears in the above-identified patent and that said Letters Patent is hereby corrected as shown below:

Column 2, line 23, -- "$10^{31\,4}$" should read -- $10^{-4}$ --.

Signed and Sealed this

Thirtieth Day of June, 1998

BRUCE LEHMAN

*Attest:*

*Attesting Officer*                *Commissioner of Patents and Trademarks*